United States Patent [19]
Duckering et al.

[11] Patent Number: 6,137,853
[45] Date of Patent: Oct. 24, 2000

[54] METHOD AND APPARATUS FOR REMOTE ULTRASONIC INSPECTION OF NOZZLES IN VESSEL BOTTOM HEAD

[75] Inventors: Brian Charles Duckering, San Jose; David Lee Richardson, Los Gatos; James Howard Terhune; Frank Ortega, both of San Jose, all of Calif.

[73] Assignee: General Electric Company, San Jose, Calif.

[21] Appl. No.: 08/322,839

[22] Filed: Oct. 13, 1994

[51] Int. Cl.[7] .................................................. G21C 17/10
[52] U.S. Cl. .............................................................. 376/252
[58] Field of Search ............................................. 376/252

[56] References Cited

U.S. PATENT DOCUMENTS

| | | | |
|---|---|---|---|
| 3,987,666 | 10/1976 | Blanc et al. | 73/67.83 |
| 3,999,423 | 12/1976 | Tyree | 73/67.88 |
| 4,311,052 | 1/1982 | Jeffras et al. | 73/634 |
| 4,463,609 | 8/1984 | Thome et al. | 73/637 |
| 4,530,242 | 7/1985 | Sandhu | 73/625 |
| 4,548,785 | 10/1985 | Richardson et al. | 376/249 |
| 4,562,738 | 1/1986 | Nakayama et al. | 73/622 |
| 5,125,274 | 6/1992 | Gilbert | 73/622 |

*Primary Examiner*—Charles T. Jordan
*Assistant Examiner*—Meena Chelliah
*Attorney, Agent, or Firm*—James E. McGinness

[57] ABSTRACT

A method and an apparatus for ultrasonically inspecting the welds which attach the differential pressure and liquid poison nozzles to the bottom head of the reactor pressure vessel in a boiling water reactor. The scanning apparatus is seated on the upper taper of the nozzle outer tube and incorporates a stationary frame having a cutaway section which allows installation from the side. The apparatus has vertical and circumferential positioning mechanisms which are operated remotely to scan an ultrasonic transducer package over the circumferential welds and heat-affected zones thereof. The rotating frame has a transducer carriage mounted thereon which is vertically displaceable relative to the rotating frame. The vertical and angular motion motors can be controlled together to provide the desired path for the ultrasonic transducer around the stub tube. The tool also includes a vessel contour follower which follows the contour of the inclined surfaces of the reactor pressure vessel bottom head. The vessel contour follower is linked to the ultrasonic transducer to ensure that the transducer follows the contour of the weld, in position and angle.

15 Claims, 8 Drawing Sheets

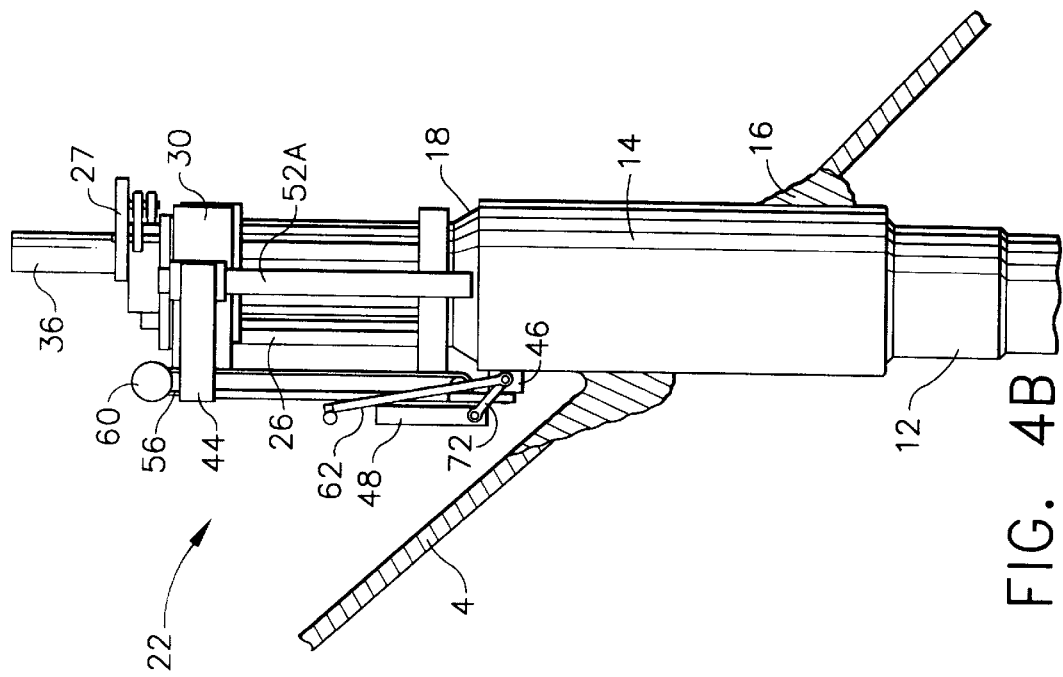
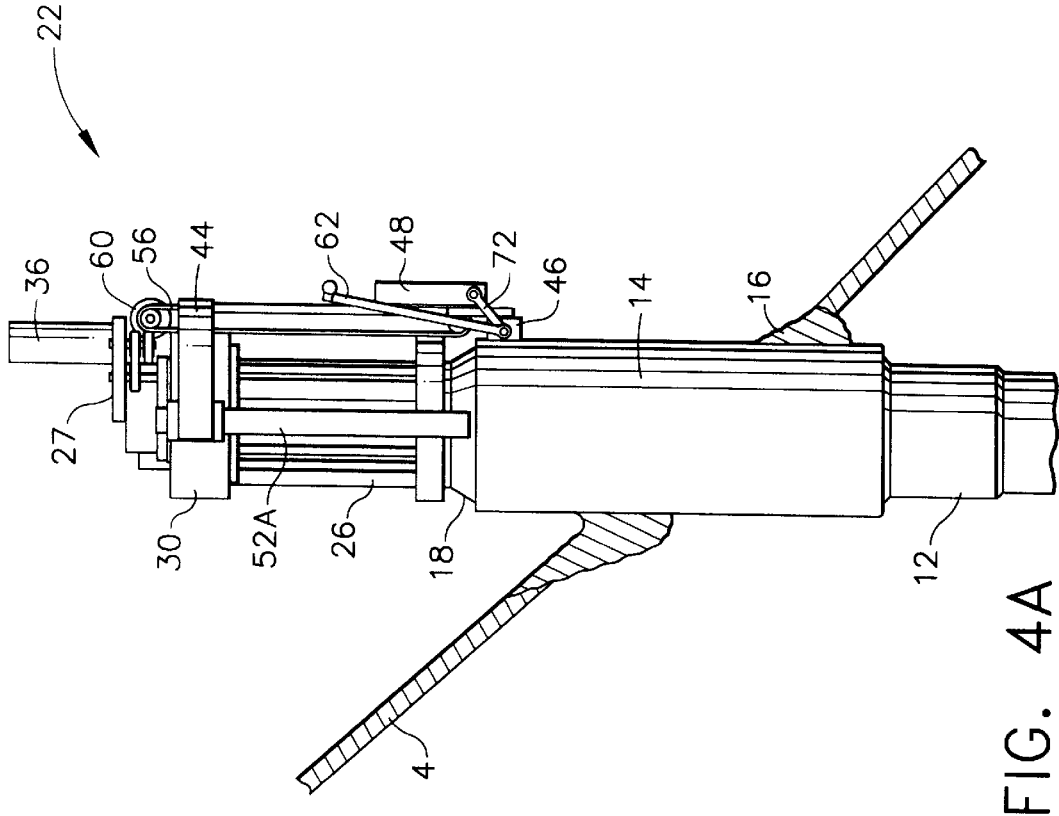

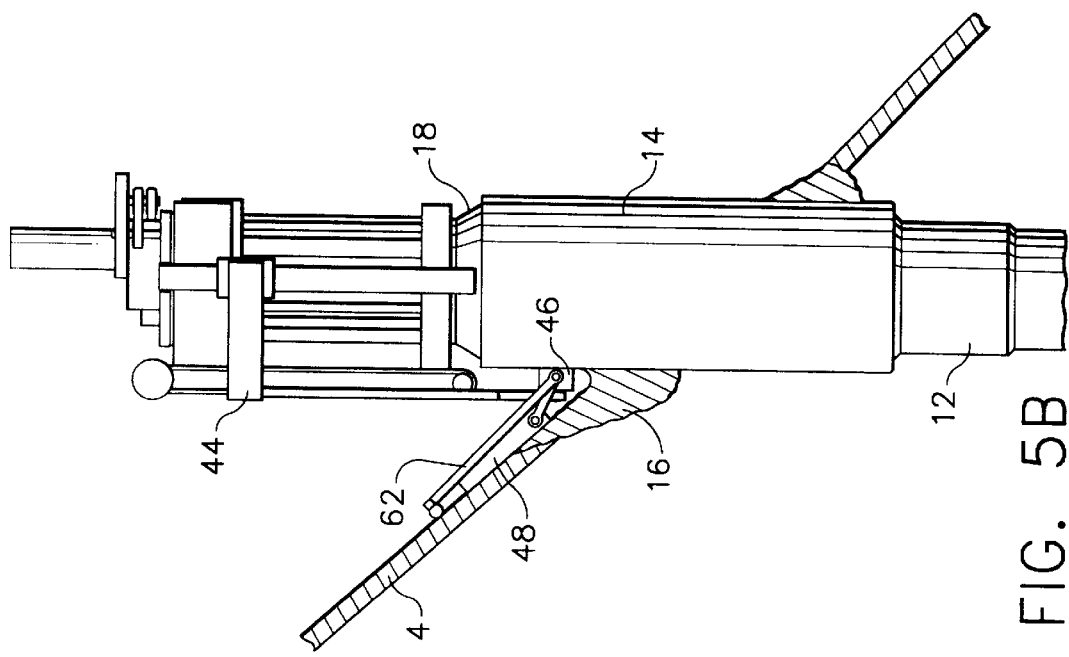
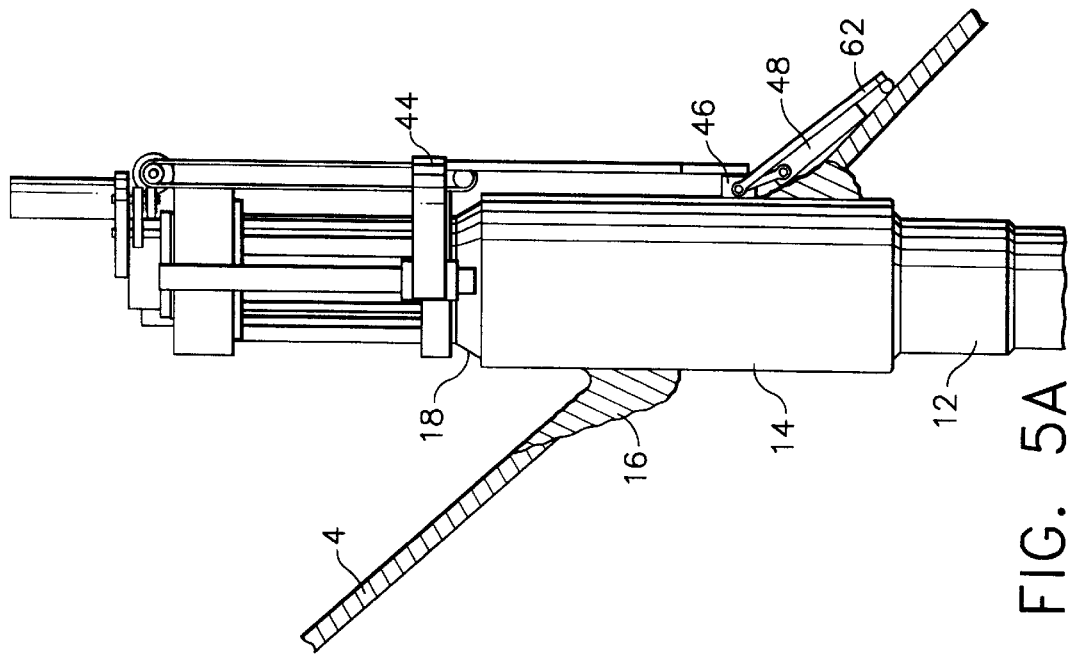
FIG. 5A
FIG. 5B

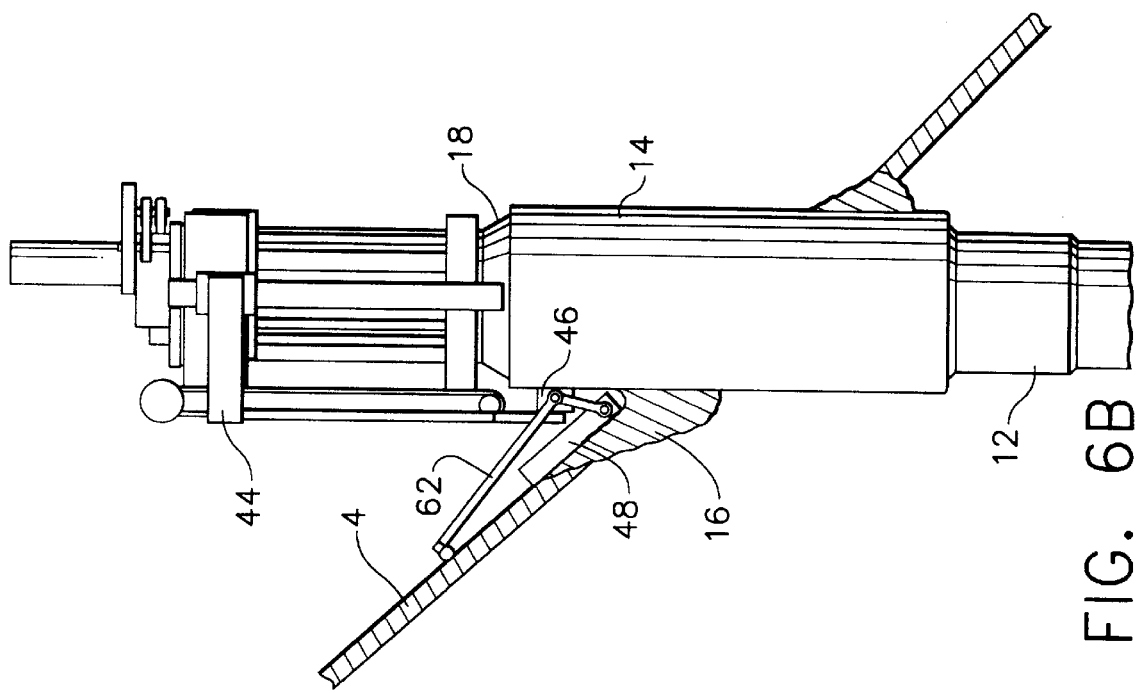
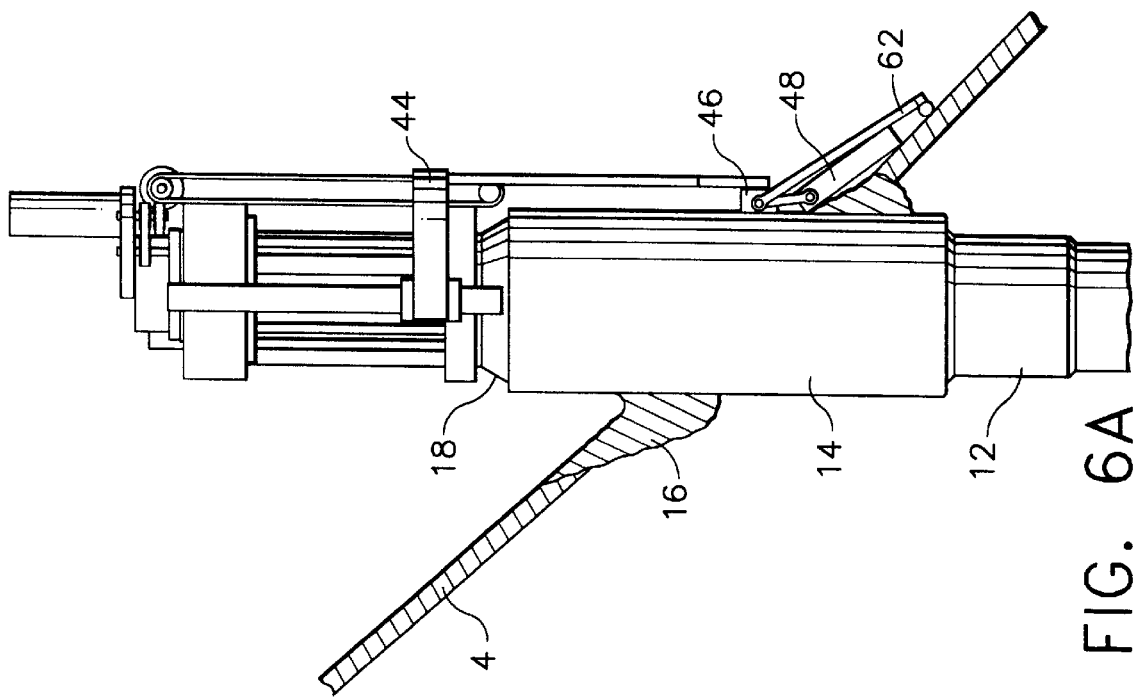

METHOD AND APPARATUS FOR REMOTE ULTRASONIC INSPECTION OF NOZZLES IN VESSEL BOTTOM HEAD

FIELD OF THE INVENTION

This invention relates generally to nondestructive examination of material, such as metal, for voids, flaws, cracks and other defects that can be detrimental to the integrity of the material. Specifically, the invention relates to the ultrasonic inspection of nozzles located high on the periphery of penetrations in the bottom head of the reactor pressure vessel of a boiling water reactor.

BACKGROUND OF THE INVENTION

The structure of a water-cooled and water-moderated nuclear reactor of the boiling water type is well known. (See, e.g., U.S. Pat. Nos. 4,548,785 and 5,118,464 to Richardson et al.) As depicted in FIG. 1, a boiling water reactor 2 includes a reactor pressure vessel 4 containing a nuclear reactor core (not shown) submerged in a coolant-moderator such as light water. The core, which is surrounded by an annular shroud 6, includes a plurality of replaceable fuel assemblies (not shown) arranged in spaced relation between an upper core support grid 8 and a lower core support plate 10. A plurality of control rod drive housings (not shown) penetrate the bottom head of the reactor pressure vessel 4 and house control rod drives by which a plurality of control rods (not shown) are selectively insertable among the fuel assemblies for controlling the core reactivity.

Each control rod and the four fuel assemblies comprise a fuel cell of the core. The four fuel assemblies are laterally supported at their upper ends in an opening in the upper core support grid 8 formed by intersecting and interlocking beams. At their lower ends the four fuel assemblies are vertically supported on the fuel assembly support member fitted to the top end of the control rod guide tube, lateral support being provided by passage of the guide tube through an aperture or hole in the lower core support plate 10.

In addition, a plurality of nozzles (only one nozzle 20 of which is shown in FIG. 1) penetrate the bottom head of the reactor pressure vessel. These nozzles are of two types: differential pressure nozzles which provide means for monitoring the differential pressure across the fuel core and liquid poison nozzles which provide means for supplying liquid neutron absorber to the fuel core in the event of a transient overpower event with inability to scram. Each nozzle 20 is supported by an outer tube 12 and extends to the elevation of the upper core support grid 8. The outer tubes 12 are affixed to bottom-head penetrations.

Penetration of the differential pressure and liquid poison nozzles through the bottom head of the reactor pressure vessel 4 is accomplished using stub tubes 14 (see FIG. 7A). Each stub tube, suitably shaped at its bottom end to fit the curvature of the bottom head at its particular location, is secured in a corresponding aperture or hole in the bottom head by a circumferential weld 16. The outer tube 12 is welded to the top end of the stub tube 14 by a circumferential weld 18 after the outer tube 12 is properly positioned vertically.

As is evident from the foregoing, the stub tubes 14 become a part of the pressure vessel boundary and any defect (e.g., cracks) therein can jeopardize the integrity of the pressure system. Under certain conditions, the stub tubes are found to undergo stress corrosion cracking in the heat-affected zone adjacent to the upper weld 18 joining the outer tube and the stub tube. This stress corrosion cracking may result in water leakage from the vessel through the narrow gap between the outer tube 12 and the stub tube 14, an undesirable event necessitating repair.

For the foregoing reasons, the welds which attach the outer tube to the reactor pressure vessel are required to be examined periodically to determine their structural integrity. However, the differential pressure and liquid poison nozzles are inherently difficult to access. Therefore, means for remotely and automatically inspecting the welds by which the differential pressure and liquid poison nozzles are attached to the reactor pressure vessel are needed.

SUMMARY OF THE INVENTION

The present invention is a method and an apparatus for ultrasonically inspecting the welds which attach the differential pressure and liquid poison nozzles to the bottom head of the reactor pressure vessel. The scanning apparatus is lowered from the refueling bridge into position around the outer tube and seated on the upper taper of the outer tube. Since there is no access to the top of outer tube when the nozzles is installed, the scanner is installed from the side. The apparatus has a cutaway section which allows installation from the side.

The apparatus incorporates a stationary frame and vertical and circumferential positioning mechanisms which are operated remotely to scan transducer means over the circumferential welds and heat-affected zones thereof. The circumferential positioning means includes a rotating frame which sits in a V-guide on the stationary frame, on which it can rotate 360°. The rotating frame has a transducer carriage mounted thereof. The transducer carriage, which carries the transducer means, is vertically displaceable relative to the rotating frame. The vertical motion path of the transducer carriage is maintained by linear slide assemblies located on opposing sides of the stationary frame. The vertical and angular motion motors can be controlled together to provide the desired path for the transducer means around the stub tube.

The invention further comprises means for following the contour of the inclined surfaces of the reactor pressure vessel bottom head. These contour following means ensure that the transducer means follow the contour of the weld, in position and angle. The vessel contour follower is a free-hinged frame with weighted rollers at the end which lay flat on the vessel surface regardless of the angle of inclination thereof. To achieve this function, the vessel contour follower is pivotably mounted on an up-and-down hinge, which is in turn mounted on a side-to-side hinge at the bottom of the transducer carriage.

BRIEF DESCRIPTION OF THE DRAWINGS

FIGS. 4A and 4B show the respective positions of the transducer packages of the ultrasonic inspection tool for the scans depicted in FIG. 7A.

FIGS. 5A and 5B show the respective positions of the transducer packages of the ultrasonic inspection tool for the scans depicted in FIG. 7B.

FIGS. 6A and 6B show the respective positions of the transducer packages of the ultrasonic inspection tool for the scans depicted in FIG. 7C.

DETAILED DESCRIPTION OF THE PREFERRED EMBODIMENTS

The invention is described herein as applied to the examination of the circumferential weld which attaches a stub tube to an outer tube concentrically arranged inside the stub tube and the circumferential weld which attaches a stub tube to the bottom head of a reactor pressure vessel. However, an artisan of ordinary skill in the art of nondestructive examination will readily appreciate that the method and apparatus of the invention are generally applicable to the detection of cracks in an outer circumferential weld on a circular cylindrical component which is inaccessible from the top.

Figure 1:
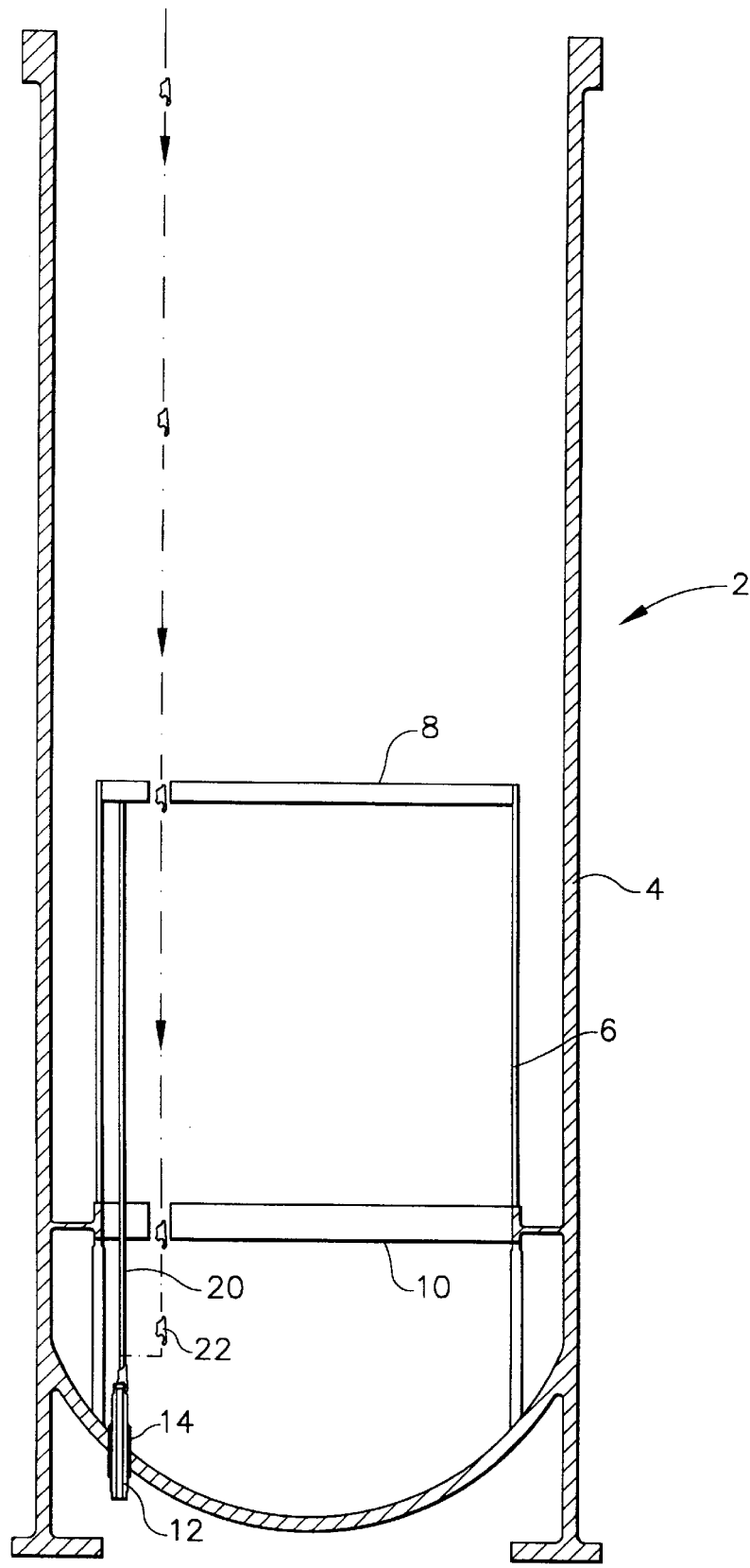
FIG. 1 is a schematic representation of the path by which the tool of the present invention is placed into required position for inspecting the welds by which a nozzle is attached to the bottom head of a reactor pressure vessel in a boiling water reactor.

To accommodate inspection of the differential pressure and liquid poison nozzles, it is necessary that reactor fuel bundles and internals be temporarily removed during outages. In particular, the four adjacent fuel assemblies nearest to the nozzles being ultrasonically inspected, the associated control rod blade and guide tube, and the associated fuel support casting must all be removed. Referring to FIG. 1, an inspection tool 22 is then lowered approximately 125 feet through the reactor water from the refueling bridge (not shown), through the top guide fuel support 8 and the lower fuel core support plate 10, and positioned on the nozzle outer tube 12 which is to have its welds inspected.

The inspection tool 22 is attached to an aluminum poling tool (not shown) with a "dog-leg" on the lower end. When manipulated properly, this curved member will allow the inspection tool to come to rest over and around the outer tube 12. The inspection tool has a cutaway section which allows installation from the side. When positioned properly, the tool will be seated on an upper circumferential taper 19 formed on the outer tube.

Figure 7A:
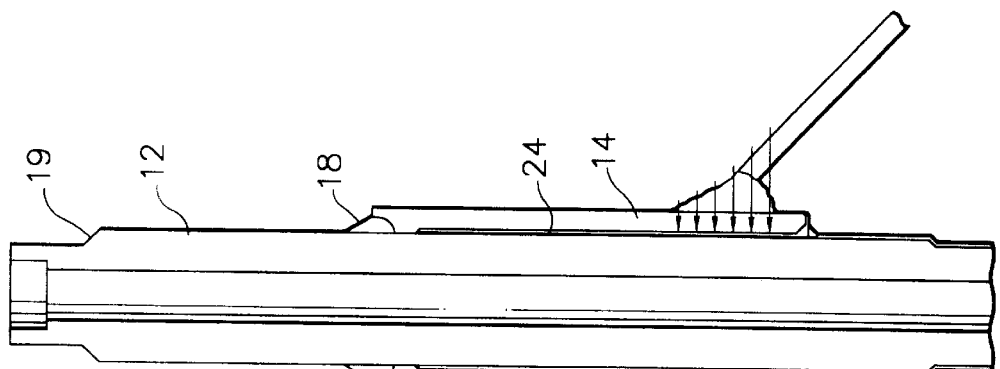
FIG. 7A shows the path of the ultrasound beams during scanning of the stub tube-to-outer tube circumferential weld and heat-affected zone thereof by the first transducer package in accordance with the preferred embodiment of the invention.

As shown in FIG. 7A, each tube 12 passes through the bottom head of the reactor pressure vessel 4. The outer tube 12 is supported by a stub tube 14. At its top end, stub tube 14 is joined to outer tube 12 by an upper circumferential attachment weld 18. At its bottom end stub tube 14 is joined to the bottom head of the reactor pressure vessel 4 by a lower circumferential attachment weld 16. The stub tube 14 and outer tube 12 are separated by a fluid-filled annular gap 24.

With respect to the differential pressure and liquid poison nozzles, the areas where examination is required are the stub tube to outer tube attachment weld 18 and heat-affected zone adjacent thereto and the stub tube to reactor pressure vessel attachment weld 16 and heat-affected zone adjacent thereto. For example, experience has shown that the heat-affected zone of the stub tube adjacent to upper weld 18 is susceptible to stress corrosion cracking. The conditions of metallic tension, stagnation of water flow and oxygen concentration can result in a radially inwardly propagating crack which will propagate along the granular boundaries of the stub tube metal. Ultimately, the crack could propagate to the inner surface of the stub tube, whereat the crack is in fluid communication with gap 24, thereby creating a flow path for water to escape from the reactor pressure vessel.

Ultrasound is a common means of nondestructively inspecting materials for flaws and structural integrity. For steels, the preferred frequency used for inspection and sizing of flaws is in the range of 1 to 10 MHz with 2.25 to 5 MHz preferred. Ultrasonic transducers and associated electronics are conventional in the art of nondestructive examination.

In accordance with conventional practice, pulsed ultrasound generated by a transducer propagates into the metal to be inspected via a coupling fluid, such as water, in contact with the surface of the metal. Discontinuities in the metal (e.g., cracks) produce ultrasonic pulse reflections, due to sudden changes in acoustic impedance, that are dependent on factors such as flaw size and shape, angle of incidence, and metal path length. These reflections are detected by ultrasonic transducers operating in a reception mode.

Figure 2A:
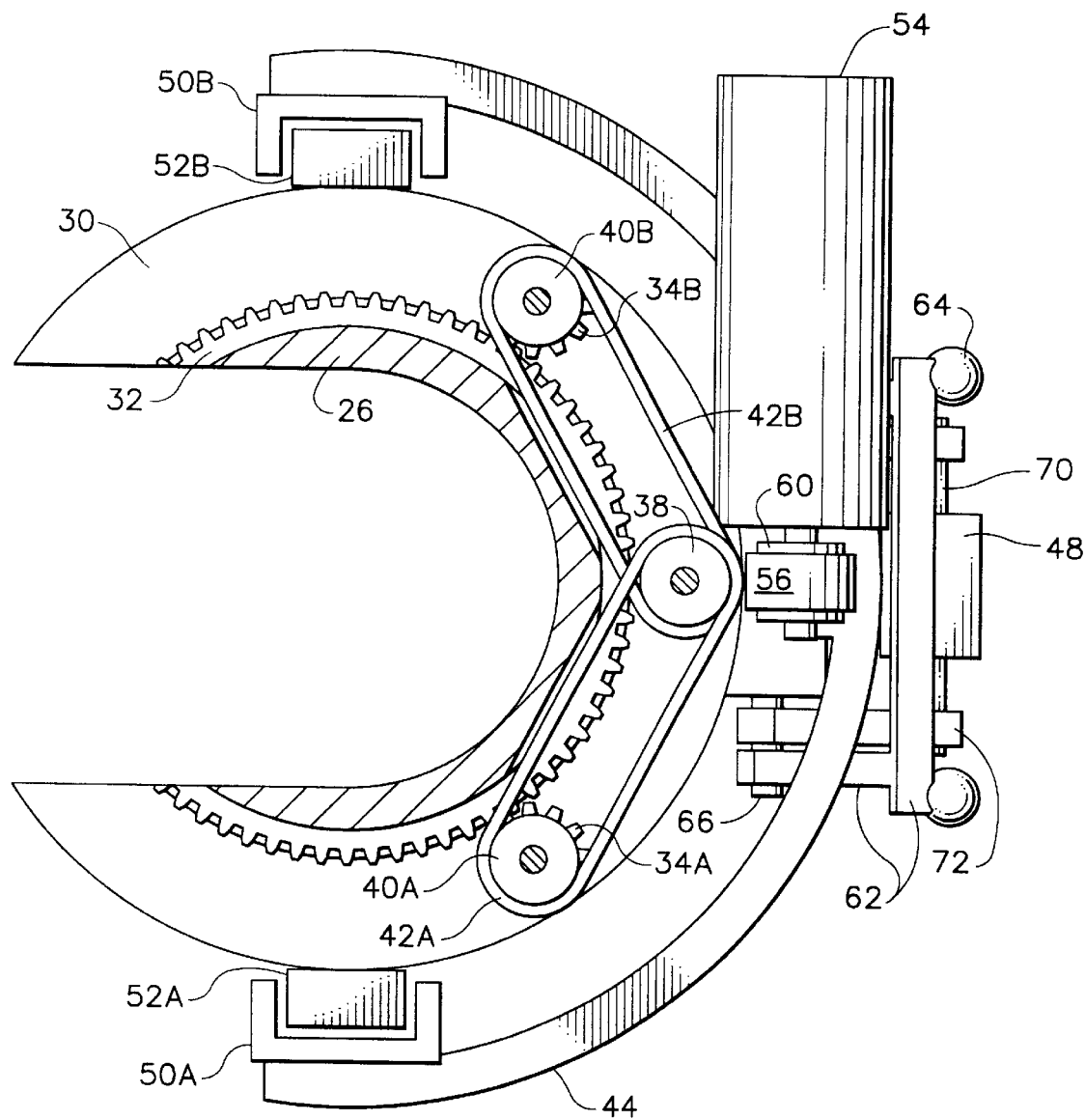
FIG. 2A is a top view of an ultrasonic inspection tool in accordance with the preferred embodiment of the invention. The angular motion motor and the top plate of the stationary frame have been removed for the sake of visibility of other parts.
Figure 2B:
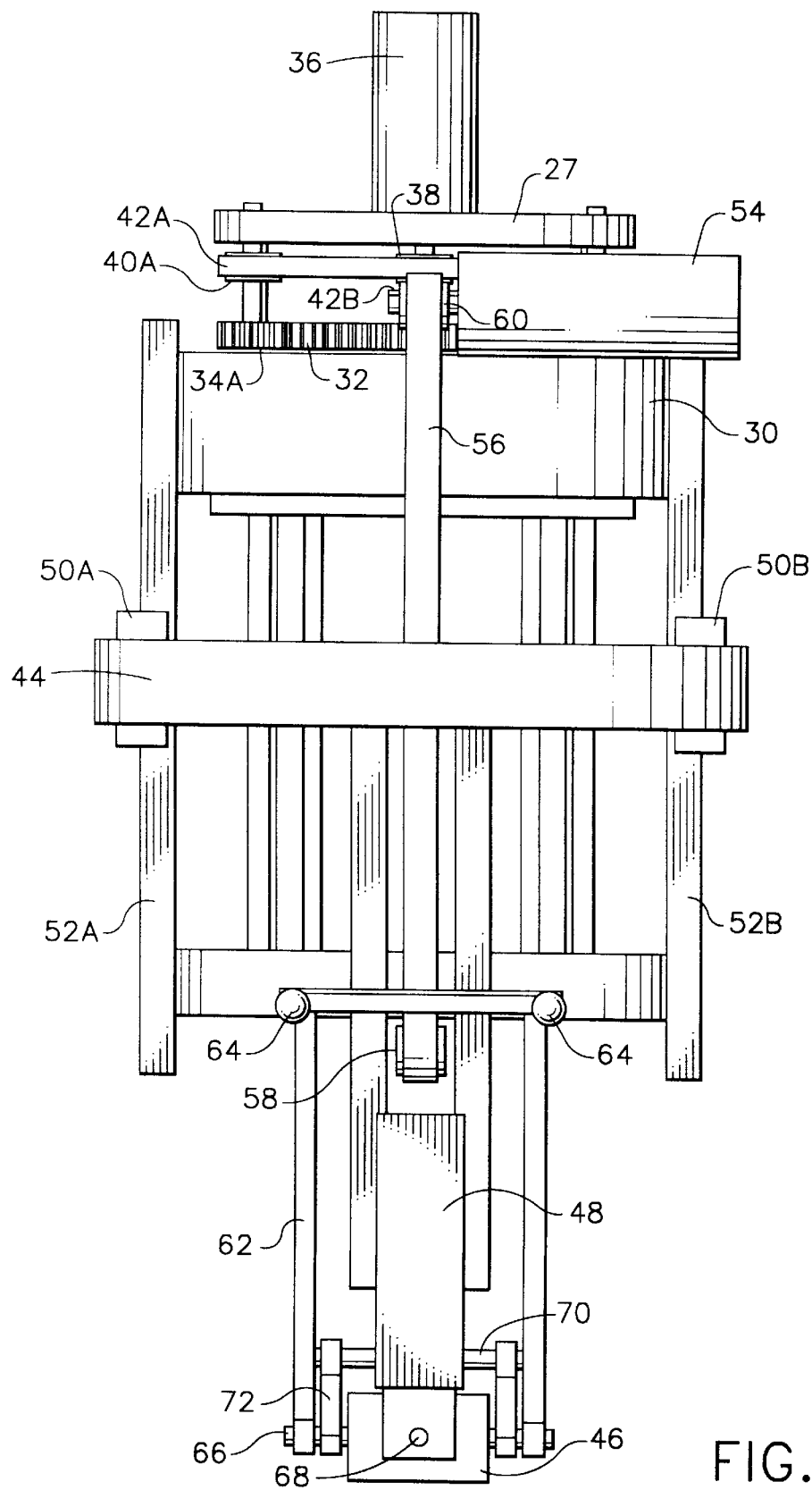
FIG. 2B is a front view of an ultrasonic inspection tool in accordance with the preferred embodiment of the invention.
Figure 3:
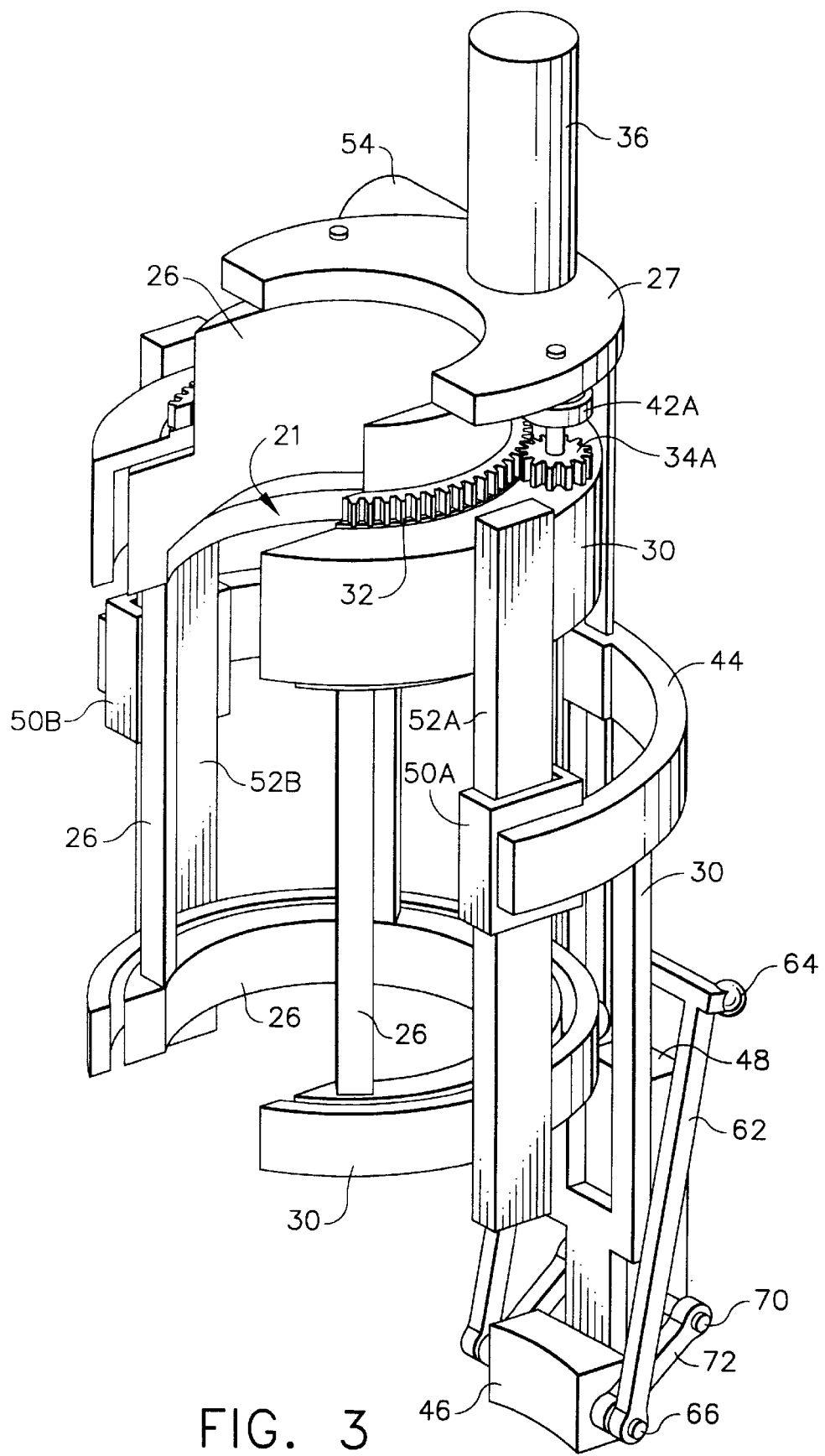
FIG. 3 is an isometric view of the ultrasonic inspection tool in accordance with the preferred embodiment of the invention.

A tool 22 for ultrasonically inspecting welds 16 and 18 and heat-affected zones thereof is shown in detail and FIGS. 2A, 2B and 3. The tool comprises a stationary frame 26 which has a cutaway section (best seen in FIG. 2A) that allows the stationary frame to be inserted on the outer tube from the side. There is a larger-diameter cutout below a shoulder on the top of the stationary frame (see FIG. 3) by means of which the tool rests on the tapered circumferential shoulder 18 seen in FIG. 7A.

The tool 22 further comprises a rotating frame 30 having a cutaway section and rotatably mounted on stationary frame 26. The rotating frame can rotate 360° about a centerline axis of the stationary frame 26. The rotating frame has upper and lower sets of V-rollers (e.g., six in each set) circumferentially distributed at equal angular intervals. Each V-roller is rotatably mounted on a respective vertical spindle. The stationary frame has corresponding upper and lower V-guides extending circumferentially around the top and bottom frame section respectively, excluding the cutout. Each V-guide is a recess disposed in a horizontal plane and having a V-shaped cross section conforming to the cross-sectional V-shape of the V-rollers. In a conventional manner, the V-rollers roll in the V-guides to facilitate rotation of the rotating frame. When the cutaway section of the stationary and rotating frames are aligned, as depicted in FIG. 2A, the tool can be installed on the outer tube.

Referring to FIG. 2A, a section of a toothed ring gear 32 is securely mounted on the rotating frame 30. A pair of drive gears 34A and 34B are rotatably mounted on the stationary frame. Each of drive gears 34A and 34B has teeth which engage the teeth on the toothed ring gear section 32. The axes of rotation of drive gears 34A and 34B are angularly spaced such that at least one of the two drive gears is in engagement with the toothed ring gear section 32 at all times. The drive gears are in turn driven to rotate by an angular motion motor 36 (see FIGS. 2B and 3) via a pulley arrangement. The pulley arrangement comprises an angular motion drive pulley 38 connected to an output shaft of the angular motion motor 36; a pair of driven pulleys 40A and 40B connected to the drive gears 34A and 34B respectively; and a pair of timing belts 42A and 42B for respectively coupling the driven pulleys 40A and 40B to the angular motion drive pulley 38. The angular motion motor 36, drive pulley 38 and driven pulleys 40A and 40B are all supported by the top plate 27 of stationary frame 26, as seen in FIGS. 2B and 3. The angular motion motor and the top plate of the stationary frame have been removed from FIG. 2A for the sake of visibility of other parts.

In response to activation of angular motion motor 36, the drive gears 34A and 34B are rotated. At least one of these drive gears will engage the toothed ring gear section 32, even when the other drive gear is located within the cutaway section and disengaged from toothed ring gear section, thereby ensuring continuous motion. The engaged drive gear(s), when driven, causes rotating frame 30 to rotate around the stationary frame 26.

The rotating frame 30 has a transducer carriage 44 mounted thereon. The transducer carriage 44, which carries the transducer packages 46 and 48 (see FIGS. 2B and 3), is vertically displaceable relative to the rotating frame. The vertical motion path of the transducer carriage is maintained by linear slide assemblies located on opposing sides of the rotating frame 30. In particular, each linear slide assembly comprises a linear slide carriage (50A and 50B) securely mounted on the transducer carriage 44 and a linear slide rail (52A and 52B) securely mounted on the rotating frame 30.

Vertical travel of the transducer carriage 44 is accomplished by a vertical motion motor 54 which drives a timing belt 56 looped over a lower pulley 58 rotatably mounted on rotating frame 30 and an upper pulley 60 connected to the output shaft of vertical motion motor 54. The timing belt is fixed to the midportion of transducer carriage 44, so that circulation of the timing belt on pulleys 58 and 60 produces vertical displacement of the transducer carriage.

The vertical and angular motion motors can be controlled together to provide the desired path for the transducer packages around stub tube. In particular, the transducer package 46 at the end of the transducer carriage 44 is the point whose position is controlled, both vertically and angularly around the tube. In addition, means are provided which follow the contour of the inclined surfaces of the reactor pressure vessel bottom head. These contour following means ensure that the transducer packages follow the contour of the weld, in position and angle, during scanning.

The vessel contour follower is stored in an up position, as shown in FIG. 2B, during installation of tool 22 and even after installation when not needed. The vessel contour follower is held in the up position by a torsion spring (not shown). To lower the vessel contour follower, the tension spring is released by remote manipulation of a service pole.

The vessel contour follower is a free-hinged U-shaped frame 62 with weighted rollers 64 at the end corners. When the vessel contour follower is lowered, the frame will lay flat on the vessel surface regardless of the angle of inclination thereof. To achieve this function, the frame 62 is pivotably mounted on an up-and-down hinge 66, which is in turn mounted on a side-to-side hinge 68 at the bottom of the transducer carriage 44. Hinge 68 has an axis which is generally radially directed.

The contour of the surface contacted by weighted rollers 64 determines the angles of tilt experienced by hinge 66. The first transducer package 46, which can be positioned to scan both attachment welds 16 and 18, is connected to hinge 66 and also pivots about side-by-side hinge 68 in response to tilting of frame 62 of the vessel contour follower. The second transducer package 48 is also coupled to up-and-down hinge 66 via a pair of links 72 and a second up-and-down hinge 70, which is disposed in parallel with up-and-down hinge 66. The transducer package 48 is double-hinged to allow both weighted rollers 64 to remain in contact with the vessel/weld regardless of angle and variations in surface. This allows transducer package 48 to adjust its orientation to compensate for surface variations in a radial direction. Since transducer package 48 is coupled to up-and-down hinge 66, which is pivotably mounted on side-to-side hinge 68, transducer package 48 is also effectively pivotably mounted on side-to-side hinge 68. This allows transducer package 48 to adjust its orientation to compensate for surface variations in a circumferential direction.

The above-described inspection tool performs ultrasonic scanning in three modes. In the first mode, depicted in FIGS. 4A, 4B and 7A, the transducer package 46 scans circumferential attachment weld 18 and the heat-affected zone thereof. FIGS. 4A and 4B respectively show the positions of transducer package 46 before and after a 180° rotation of rotating frame 30. The arrows in FIG. 7A depict the scanning of weld 18 and heat-affected zones thereof located in outer tube 12 and stub tube 14.

Figure 7B:
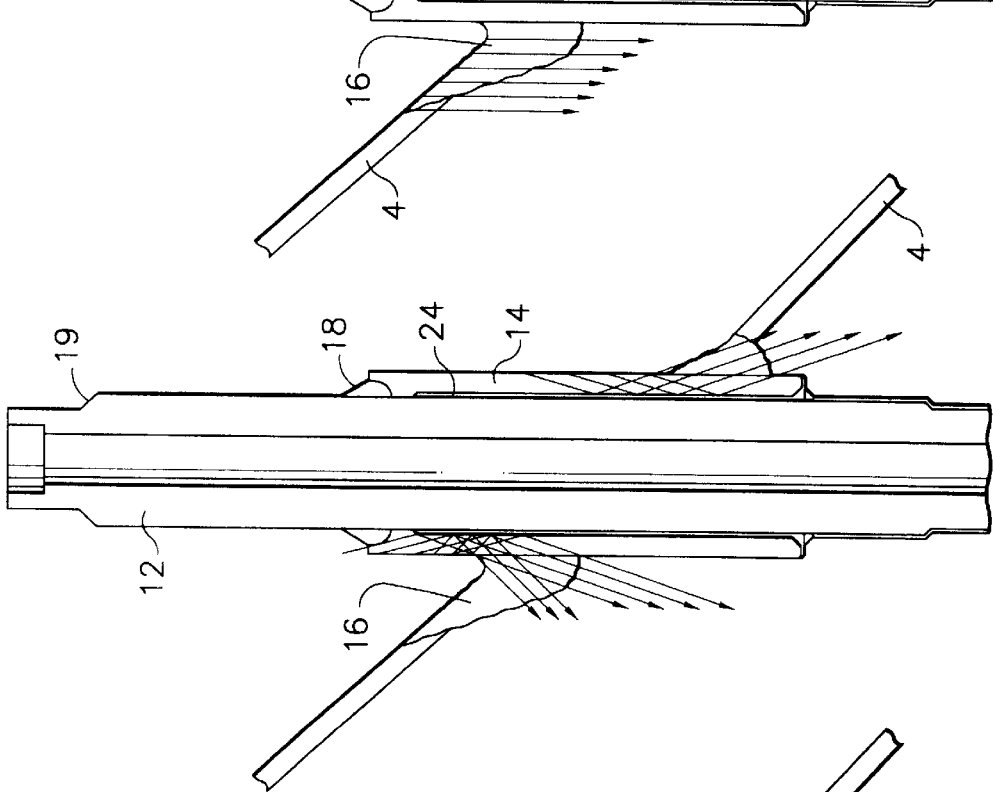
FIG. 7B shows the path of the ultrasound beams during scanning of the stub tube-to-reactor pressure vessel circumferential weld and heat-affected zone thereof by the first transducer package.

In the second mode, depicted in FIGS. 5A, 5B and 7B, the transducer package 46 scans circumferential attachment weld 16 and the heat-affected zone thereof while the vessel contour follower is down. FIGS. 5A and 5B respectively show the positions of transducer package 46 before and after a 180° rotation of rotating frame 30 which is accompanied by vertical displacement of transducer package 46. The arrows in FIG. 7B depict the scanning of weld 16 and heat-affected zones thereof located in stub tube 14.

Figure 7C:
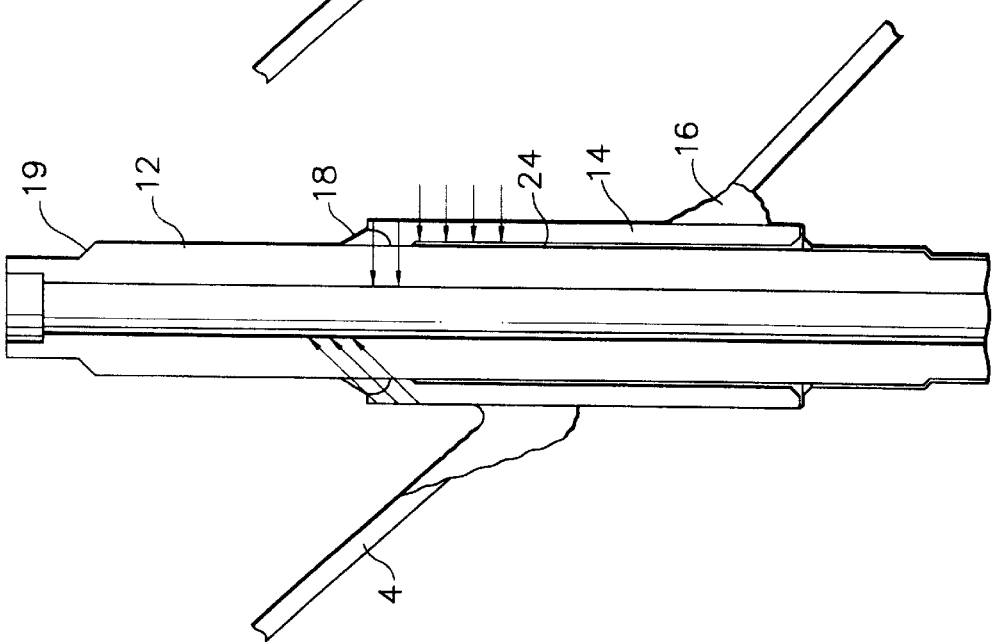
FIG. 7C shows the path of the ultrasound beams during scanning of the stub tube-to-reactor pressure vessel circumferential weld and heat-affected zone thereof by the second transducer package in accordance with the preferred embodiment of the invention.

In the third mode, depicted in FIGS. 6A, 6B and 7C, the transducer package 48 scans circumferential attachment weld 16 and the heat-affected zones thereof while the vessel contour follower is down. FIGS. 6A and 6B respectively show the positions of transducer package 48 before and after a 180° rotation of rotating frame 30 which is accompanied by vertical displacement of transducer package 46. The arrows in FIG. 7C depict the scanning of weld 16 and a heat-affected zones thereof located in stub tube 14.

In the second and third scanning modes, the transducers will follow the contour of attachment weld 16 in position and angle.

The foregoing preferred embodiment has been disclosed for the purpose of illustration. Variations and modifications which do not depart from the broad concept of the invention will be readily apparent to those skilled in the design of ultrasonic inspection equipment. For example, vertical travel of the transducer carriage can be accomplished using a conventional ball screw in place of a timing belt. Rollers could be substituted for the slide rails. The angular motion motor, drive pulley and driven pulleys could be mounted on the rotating frame and the toothed ring gear section could be mounted on the stationary frame. All such variations and modifications are intended to be encompassed by the claims set forth hereinafter.

What is claimed is:

1. An inspection apparatus comprising:
    a stationary frame having a cutaway section and a centerline axis;
    a rotating frame having a cutaway section and rotatably mounted on said stationary frame, said rotating frame being rotatable about said centerline axis and comprising first and second linear rails arranged parallel to said centerline axis;

carriage means which are translatable along said first and second linear rails, respectively;

means for translating said carriage means along said first and second linear rails, respectively; and ultrasonic transducer means mounted on said carriage means, wherein said cutaway sections are aligned when said rotating frame is located in a predetermined angular position relative to said stationary frame.

2. The inspection apparatus as defined in claim 1, wherein said rotating frame is rotatably mounted on said stationary frame via a plurality of rollers.

3. The inspection apparatus as defined in claim 1, further comprising a section of a toothed ring gear which is securely mounted on said rotating frame, and first and second drive gears which are rotatably mounted on said stationary frame, each of said first and second drive gears having teeth which engage said toothed ring gear section when said cutaway sections are aligned, said rotating frame being rotatable 360° around said centerline axis, the axes of rotation of said first and second drive gears being angularly spaced such that at least one of said first and second drive gears is in engagement with said toothed ring gear section at all times.

4. The inspection apparatus as defined in claim 3, further comprising an angular motion motor, an angular motion drive pulley coupled to said angular motion motor, first and second driven pulleys coupled to said first and second drive gears respectively, and first and second belts for coupling said first and second driven pulleys to said angular motion drive pulley, wherein said angular motion motor and said angular motion drive pulley are mounted on said stationary frame.

5. The inspection apparatus as defined in claim 1, wherein said carriage means comprise first and second linear carriages which are translatable along said first and second linear rails respectively.

6. The inspection apparatus as defined in claim 1, further comprising first hinge means coupled to said carriage means and having a first hinge axis which lies in a generally radial direction, said ultrasonic transducer means being freely pivotable about said first hinge axis.

7. The inspection apparatus as defined in claim 6, further comprising second hinge means having a second hinge axis which is perpendicular to said first hinge axis and to said centerline axis, and contour follower means coupled to said second hinge means, said contour follower means being freely pivotable about said second hinge axis and said second hinge axis being freely pivotable about said first hinge axis.

8. The inspection apparatus as defined in claim 7, further comprising third hinge means having a third hinge axis which is parallel to said second hinge axis, said third hinge means being pivotable about said second hinge axis and said ultrasonic transducer means being pivotable about said third hinge axis.

9. An inspection apparatus comprising:

a stationary frame having a centerline axis;

a rotating frame rotatably mounted on said stationary frame, said rotating frame being rotatable about said centerline axis;

carriage means translatably mounted on said rotating frame;

first pivotable means pivotably mounted on said carriage means, said first pivotable means being freely pivotable about a first pivot axis which lies in a generally radial direction;

second pivotable means pivotably mounted on said first pivotable means, said second pivotable means being freely pivotable about a second pivot axis which lies perpendicular to said first pivot axis; and first ultrasonic transducer means coupled to said second pivotable means, whereby said first ultrasonic transducer means are freely pivotable about said first and second pivot axes.

10. The inspection apparatus as defined in claim 9, further comprising third pivotable means pivotably mounted on said second pivotable means, said third pivotable means being pivotable about a third pivot axis parallel to said second pivot axis, wherein said first ultrasonic transducer means are mounted on said third pivotable means and are pivotable about said third pivot axis.

11. The inspection apparatus as defined in claim 9, further comprising contour follower means pivotably mounted on said second pivotable means, said contour follower means being freely pivotable about said first and second pivot axes.

12. The inspection apparatus as defined in claim 11, wherein said contour follower means comprise a U-shaped frame pivotably mounted on said second pivotable means, and first and second rolling means rotatably mounted on said U-shaped frame.

13. The inspection apparatus as defined in claim 10, further comprising second ultrasonic transducer means mounted on said first pivotable means, whereby said second ultrasonic transducer means are pivotable about said first pivot axis but not said second pivot axis.

14. The inspection apparatus as defined in claim 10, wherein said rotating frame comprises first and second linear slide rails, and said carriage means comprise first and second linear slide carriages which are slidable along said first and second linear slide rails respectively.

15. The inspection apparatus as defined in claim 10, further comprising first drive means for rotating said rotating frame relative to said stationary frame, and second drive means for translating said carriage means relative to said rotating frame.

* * * * *